(12) United States Patent
Asafusa

(10) Patent No.: US 6,866,634 B2
(45) Date of Patent: Mar. 15, 2005

(54) ULTRASONIC DIAGNOSTIC APPARATUS

(75) Inventor: Katsunori Asafusa, Matsudo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/275,715

(22) PCT Filed: May 9, 2001

(86) PCT No.: PCT/JP01/03867

§ 371 (c)(1),
(2), (4) Date: Jul. 14, 2003

(65) Prior Publication Data

US 2004/0102700 A1 May 27, 2004

(30) Foreign Application Priority Data

May 9, 2000 (JP) ........................................ 2000-135943

(51) Int. Cl.$^7$ ................................................ A61B 8/00
(52) U.S. Cl. ...................................... 600/447; 128/916
(58) Field of Search ............................... 600/437, 443, 600/447, 454–456; 73/625–626; 367/103–105

(56) References Cited

U.S. PATENT DOCUMENTS

| | | | | | |
|---|---|---|---|---|---|
| 4,456,982 | A | * | 6/1984 | Tournois | 367/11 |
| 4,855,961 | A | * | 8/1989 | Jaffe et al. | 367/7 |
| 5,675,554 | A | * | 10/1997 | Cole et al. | 367/138 |
| 6,159,153 | A | * | 12/2000 | Dubberstein et al. | 600/443 |
| 6,277,073 | B1 | * | 8/2001 | Bolorforosh et al. | 600/437 |
| 6,537,220 | B1 | * | 3/2003 | Friemel et al. | 600/447 |
| 6,544,175 | B1 | * | 4/2003 | Newman | 600/437 |
| 6,716,173 | B2 | * | 4/2004 | Satoh | 600/447 |

FOREIGN PATENT DOCUMENTS

| | | | |
|---|---|---|---|
| JP | 1-164354 | * | 6/1989 |
| JP | 4-254754 | * | 9/1992 |
| JP | 8-38473 | * | 2/1996 |

* cited by examiner

*Primary Examiner*—Francis J. Jaworski
(74) *Attorney, Agent, or Firm*—Antonelli, Terry, Stout & Kraus, LLP

(57) ABSTRACT

An ultrasonic diagnostic apparatus is capable of displaying a three-dimensional image by performing three-dimensional scanning in an object with ultrasonic beams at rapid speed. Small transducer blocks are formed through selective connection on a two-dimensional transducer array of an ultrasonic probe. Driving pulse signals are modulated and these driving pulse signals, each having respectively different frequencies, are simultaneously provided to the selected small transducer blocks, causing said small transducer blocks to transmit ultrasonic beams to the interior of the object. Waves reflected from the interior of the object are received by each small transducer block. After the echo signals received by each small transducer block are demodulated, these signals are input to a phasing circuit to generate a plurality of received beam signals. The selected position of the small transducer blocks is moved at each repetition of ultrasonic transmission/repetition. The received beam signals are then image-processed image data, and thus displayed on a display.

7 Claims, 4 Drawing Sheets

ULTRASONIC DIAGNOSTIC APPARATUS

FIELD OF THE INVENTION

The present invention relates to an ultrasonic diagnostic apparatus of the type used in the field of the medical image diagnosis; and, more particularly, the invention relates to an ultrasonic diagnostic apparatus that can perform three-dimensional scanning at rapid speed in an object to be examined.

BACKGROUND OF THE INVENTION

In the field of the medical image diagnosis, there has been an increasing demand in recent years for diagnosing the interior of an object by taking a three-dimensional image of the object for observation, not excepting the field of ultrasonic diagnosis. The diagnosis using three-dimensional images has been developed especially in the field of the X-ray CT apparatus using X-rays and of the magnetic resonance imaging apparatus using nuclear magnetic resonance. But, the development of three-dimensional imaging has been delayed in the field of the ultrasonic diagnosis because an ultrasonic diagnostic apparatus performs scanning with ultrasonic beams having a propagation velocity in a living body which is as slow as approximately 1,500 m/s, and so it takes a long time to take a three-dimensional image of the interior of an object, since such a three-dimensional image requires a far greater number of beams, in comparison with a conventional cross sectional image that is made from approximately 100 beams.

Further, to perform three-dimensional scanning with ultrasonic beams in the object, a method of manually or mechanically moving a probe having one-dimensional built-in transducers on the surface of the object has been proposed. However, it is difficult to actually use this method, since the surface of the object is uneven, which is a second reason for the delay of development of the ultrasonic three-dimensional imaging.

As described above, the propagation velocity of ultrasound in a living body is approximately 1,500 m/s, and so a conventional cross-sectional image of the examined region can be displayed at a frame rate of 30 frames/s. Here, the number of ultrasonic scanning lines used for forming the cross sectional image is about 100. If a three-dimensional image is to be obtained with 100 scanning lines, it is necessary to narrow the scanning area, or to expand the interval between scanning lines if the scanning area is not narrowed. However, even if these methods were employed in an ultrasonic diagnostic apparatus, this apparatus could not be used for an actual diagnosis. To perform high-speed scanning on the object in real time, there are proposed a method of obtaining several beams to be received with one transmission of one ultrasonic beam and a method of transmitting ultrasonic beams in several directions at one time. However, there is a limit to the increase in processing speed obtainable by the former method. In the latter method, there is a problem that one ultrasonic beam interferes with another beam if the simultaneously transmitted beams approach each other; that is, there is a problem in that a transducer or a group of transducers may receive a reflected wave of the ultrasonic beam transmitted by the adjoining transducer or group of transducers. Therefore, the above-described conventional technology has not achieved the objective to perform three-dimensional measurement using ultrasonic beams in the object at rapid speed.

However, since various kinds of methods of producing a two-dimensional probe using a fine processing technology have been recently developed, it is becoming possible to perform three-dimensional scanning with ultrasonic beams in an object by using an electrical scanning method, without moving the probe on the surface of the object.

In the conventional technology, as described above, it takes a very long time to perform a measurement by three-dimensional scanning using ultrasonic beams in an object. The object cannot move throughout the measurement, which puts a great burden on the object. Moreover, it is difficult to observe a three-dimensional image in real time, since the procedure requires a long measurement time. These problems have not been solved at this stage of development, and an early solution of them is desired.

The present invention has been made in consideration of the above-described circumstances. The first object of the present invention is to provide an ultrasonic diagnostic apparatus that can perform three-dimensional scanning with ultrasonic beams at rapid speed.

And, the second object of the present invention is to provide an ultrasonic diagnostic apparatus that can promptly display an ultrasonic three-dimensional image.

SUMMARY OF THE INVENTION

As an embodiment of the present invention, to achieve the first object stated above, an ultrasonic diagnostic apparatus is provided, which comprises: an ultrasonic probe on which a plurality of ultrasonic transducers are arranged along a two-dimensional plane or a three-dimensional curved surface; a transducer group selecting circuit for selecting a transducer group among said plurality of transducer groups at different positions on said transducer-arranged surface; transmitting and receiving means for sending transmitted signals having characteristics which are different from each other to each of the transducer groups selected by said transducer group selecting circuit so as to transmit ultrasonic beams at one time from each transducer group to the interior of the object and then receive the resulting echo signals; and means for changing the position of the selected transducer group at every repetition of the ultrasonic transmission/reception by controlling said selecting circuit, and for performing three-dimensional scanning with ultrasound within the object by transmitting and receiving the ultrasonic beams, while controlling said transmitting and receiving means.

As an embodiment of the present invention, to achieve the second object stated above, an ultrasonic diagnostic apparatus is provided, which comprises: an ultrasonic probe on which a plurality of ultrasonic transducer groups are arranged along a two-dimensional plane or a three-dimensional curved surface; a transducer group selecting circuit for selecting a transducer group among said plurality of transducer groups at different positions on said transducer-arranged surface; transmitting and receiving means for sending transmitted signals having characteristics which are different from each other to each of the transducer groups selected by said transducer group selecting circuit so as to transmit ultrasonic beams at one time to the interior of the object and then receive the echo signals; means for changing the position of the transducer group selected at each repetition of the transmission/reception of said ultrasound by controlling said selecting circuit; means for extracting the received beam signals that match the characteristics of the signals transmitted by each of said transducer groups from among the echo signals received by said transducer groups; image composing means for composing the above-extracted received beam signals to form data for one image; and an image display for displaying an image based on the image signals output by said image composing means.

As another embodiment of the present invention to achieve the second object stated above, an ultrasonic diagnostic apparatus is provided, which comprises: an ultrasonic probe on which a plurality of ultrasonic transducers are arranged along a two-dimensional plane or a three-dimensional curved surface; a transducer group selecting circuit for selecting a transducer group among said plurality of transducer groups at different positions on said transducer-arranged surface; transmitting and receiving means for sending transmitted signals having characteristics which are different from each other to each of the transducer group selected by said transducer group selecting circuit so as to transmit ultrasonic beams at one time to the interior of the object and then receives the resulting echo signals; means for changing the position of the selected transducers at each repetition of the ultrasonic transmission/reception by controlling said selecting circuit; means for forming received beam signals, the characteristics of all of which are uniform, by using the echo signals received by said each of said transducer groups; image composing means for composing the received beam signals whose characteristics are uniform to form the sole image data; and an image display for displaying an image based on the image signals output by said image composing means.

In the above-described embodiments, the two-dimensional transducers are divided into a plurality of transducer groups, and still smaller transducer groups are selected in the divided transducer groups for transmitting and receiving ultrasonic beams. These small transducer groups are switched and selected, and thus the position thereof is moved with each repetition of ultrasonic transmission and repetition. Transmitted signals, each of which has different characteristics, for example, signals having different frequency characteristics due to modulation, are supplied, respectively, to each of the selected small transducer groups, and, thus, all of the small transducer groups simultaneously transmit ultrasonic beams having characteristics that are different from each other. Since a plurality of ultrasonic beams can be simultaneously transmitted (received) to (from) the interior of the object in this way, a three-dimensional scanning of the object can be performed at rapid speed in the object. The received signals are subject to demodulation and then to image processing to form a three-dimensional image, which is displayed on the display device. In this way, the interior of the object is three-dimensionally imaged at rapid speed.

BEST MODE FOR CARRYING OUT THE INVENTION

Figure 1:
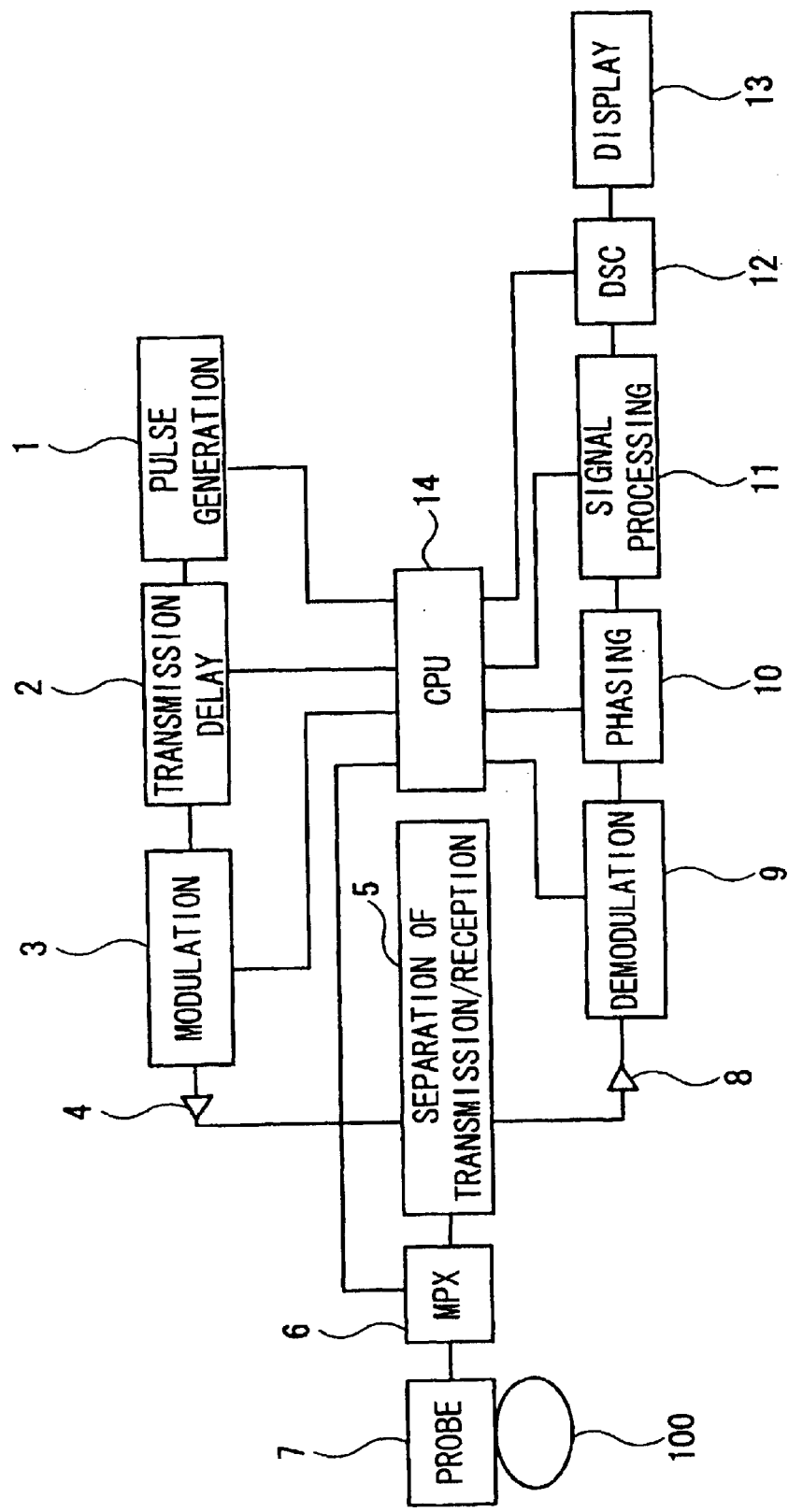
FIG. 1 is a block diagram showing the structure of an ultrasonic diagnostic apparatus representing an embodiment of the present invention.

Hereinafter, an embodiment of the present invention will be described with reference to the drawings. As seen in FIG. 1, the ultrasonic diagnostic apparatus includes a pulse generating circuit 1 for generating pulse signals to be transmitted to the ultrasonic transducers so as to transmit ultrasound to the interior of the object. A transmission delay circuit 2 receives the pulse signal output by the pulse generating circuit 1 and applies a predetermined delay time to the pulse signal applied to each driven transducer, this transmission delay circuit being comprised of a plurality of delay circuits. A modulator 3 performs a modulation process, that is, frequency modulation in this embodiment on the output signals of the transmission delay circuit 2, and an amplifier 4 is provided for amplifying the pulses generated by the pulse generation circuit 1 up to the level required for driving the transducer. A transmission/reception separating circuit 5 passes the driving pulses to the respective transducers to effect transmission of an ultrasound and passes the received echo signals to the receiver circuit in reception. A switching circuit 6 (that is, a multiplexer, hereinafter abbreviated as an MPX) is provided for switching the input/output line for the two-dimensional transducer array on the probe. Assuming that the two-dimensional transducers are formed as an array of M×N transducers, M transducers being arranged in one direction and N transducers being arranged in another direction perpendicular to said one direction, said switching circuit, for example, divides this two-dimensional array of transducers into four blocks, each comprising M/2×N/2 transducers, and performs selective connection of an m×n small-block transducer group within each block for transmitting and receiving an ultrasound, the selection of these small transducer blocks being moved at each repetition of ultrasonic transmission and reception by said MPX 6. An ultrasonic probe 7, having a large number of minute transducers, is arranged on a two-dimensional plane or a three-dimensional curved surface. The frequency characteristics of these minute transducer elements correspond to a predetermined frequency bandwidth.

A reception amplifier 8 is provided for amplifying weak echo signals output by the transducers, and a demodulator 9 is provided for demodulating the echo signals input by the amplifier 8. A reception phasing unit 10, which is comprised of a plurality of delay circuits and an adder circuit for adding the output of said delay circuits, for example, operates to form the respective received beams of said four blocks with the echo signals received by the selected small transducer block comprising m×n transducers that are respectively selected from said four blocks. A signal processing unit 11 performs preprocessing on the echo signals, such as detection processing, logarithmic compression, filtering, and γ conversion, when forming image data. An image data forming unit 12 is provided, which is comprised of a digital image memory and a control circuit for writing and reading the signal in the digital image memory. The image data forming unit 12 is referred to as a digital scan converter (DSC) in this field. An image displaying unit 13 having a three-dimensional image forming circuit is provided for forming a three-dimensional image of the image data that is read from the DSC 12. This three-dimensional image data is read out from the three-dimensional image forming circuit and converted into luminance signals and provided with hues to display the ultrasonic image on a display, such as a picture on a monitor TV. Finally, a central processing unit (CPU) 14 is provided for controlling the above-described components.

Figure 2:
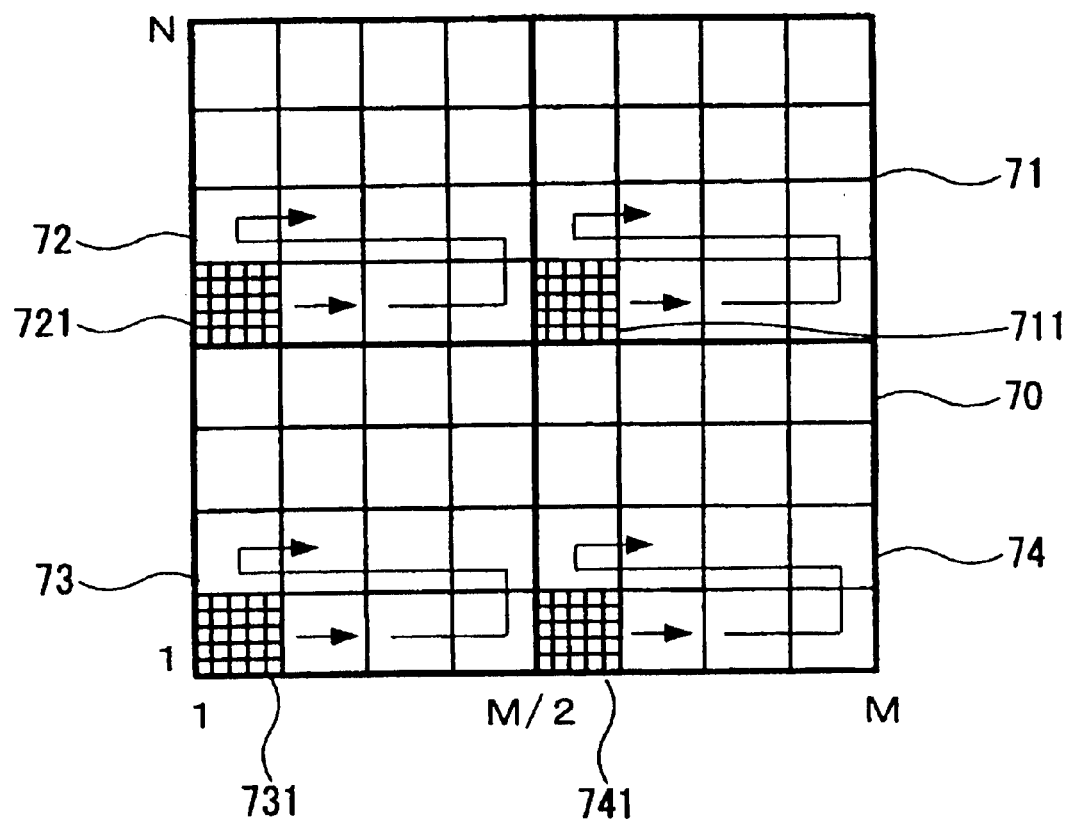
FIG. 2 is a diagram illustrating the operation of ultrasonic transmission/reception by two-dimensional transducers in accordance with the present invention.

Next, a method of ultrasonic scanning using the two-dimensional transducer array of this embodiment will be described. FIG. 2 is a diagrammatic top view of an example of the two-dimensional transducer array 70 used in this embodiment. On the plane surface of the two-dimensional transducer array 70, M×N minute transducer elements are arranged, M of said transducer elements being arranged in one direction and N of said transducer elements being arranged in the perpendicular direction. The two-dimensional transducer array 70 is divided into four large blocks, each comprising M/2×N/2 transducer elements. In each of these large blocks of transducers, a small transducer block group comprising m×n transducers is selected, m transducers being arranged in the direction in which said M transducers are arranged, and n transducer being arranged in the direction in which N transducers are arranged. These selected blocks of transducers simultaneously perform the operation of transmission/reception and ultrasonic beam scanning.

That is, as shown in FIG. 2, the two-dimensional transducer array 70 having M×N transducers is divided into large transducer blocks 71, 72, 73, and 74 having M/2×N/2 transducers. Further, in these large transducer blocks 71, 72, 73, and 74, the small transducer blocks 711, 721, 731, and 741 having m×n transducers are selected respectively. When these small transducer blocks 711, 721, 731, and 741 first transmit or receive an ultrasound, the position of them is selected as shown in FIG. 2, and the position is shifted by one element or plural elements in the direction of the arrow at each repetition of ultrasonic transmission/reception. Thus, these small transducer blocks are selected in the order in which they are sequentially moved from the initially selected position to the right edge. When the small transducer block selected in each large transducer block reaches the right edge of a large block, the ultrasonic beam scanning is performed for several cross sections, and, thus, the image data for several cross sectional images is obtained. After each small transducer block reaches the right edge of the large transducer block, the next ultrasonic transmission/reception is performed by the small transducer blocks having a position which is shifted upward by one or several elements from the initially selected position shown in the figure. And then, this small transducer block is sequentially selected to move rightward at each repetition of ultrasonic transmission/reception. The small transducer block of a shifted position is selected according to the transducer selective signal that is output by the CPU 14 to the MPX 6. In this way, the small transducer blocks are selected on the two-dimensional transducer array 70, and these small transducer groups are made to simultaneously perform ultrasonic transmission/reception, and, in addition, the position of said small transducer blocks is sequentially moved each time the ultrasonic transmission/reception is performed. Thus, ultrasonic three-dimensional scanning of the object can be performed at rapid speed.

Figure 3:
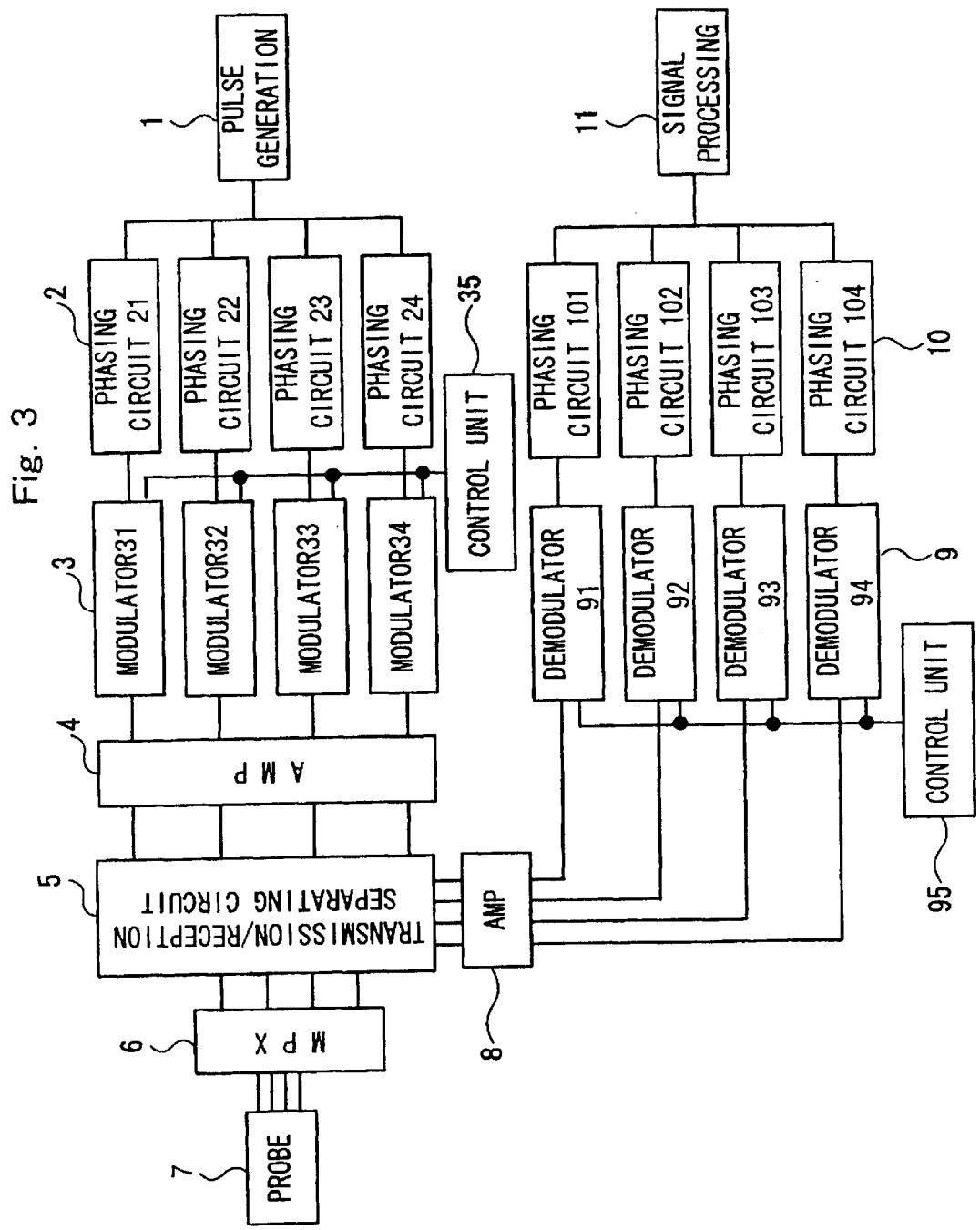
FIG. 3 is a block diagram illustrating in more detail the features of the structure illustrated in FIG. 1.

Next, a characteristic of the present invention will be described, in which, when several ultrasonic beams are simultaneously transmitted to the interior of the object, each beam is able to convey different particular information. FIG. 3 shows an example of the detailed structure of the features of the transmission/reception system provided in the ultrasonic diagnostic apparatus illustrated in FIG. 1. In FIG. 3, the pulse generating circuit 1 supplies pulses to the transmission delay circuit 2, which is comprised of four delay circuits 21, 22, 23, and 24, for applying a delay time, respectively, to each of the small transducer blocks 711, 721, 731, and 741 selected, respectively, from the four large transducer blocks 71, 72, 73, and 74 on said two-dimensional transducer array 70. Each of these delay circuits 21, 22, 23, and 24 comprises m×n (channels of) delay circuits. The frequency modulator 3 comprises four frequency modulator systems 31, 32, 33, and 34, and the outputs of said four delay circuits are input respectively, to said frequency modulators, which modulators output signals having a frequency that is different from that of the input signals. These frequency modulators 31, 32, 33, and 34 can be provided either upstream or downstream of the transmission delay circuit 2. However, the characteristics of the delay circuits 21, 22, 23, and 24 can be unified by providing said modulators downstream of the delay circuits. A control unit 35 is provided for controlling each of the frequency modulators 31, 32, 33, and 34.

The output signals of the frequency modulators are applied through the above-described amplifier 4, the transmission/reception separating circuit 5 and the MPX 6 to the probe 10, which comprises the two-dimensional transducer array 70. The reception amplifier 8 supplies the echo signals received by the probe 10 via the MPX 6 and the transmission/reception separating circuit 5 to the demodulator comprising four demodulators 91, 92, 93, and 94, each of which has m×n demodulators. These demodulators 91, 92, 93, and 94 demodulate the echo signals received by the two-dimensional transducer array 70. These circuits can be provided either upstream or downstream of the phasing circuit. However, the characteristics of four phasing circuits can be unified by providing the demodulator on the first part of the phasing circuits. The phasing circuit 10 for reception comprises four phasing circuits of 101, 102, 103, and 104, each of which has m×n (channels of) phasing circuits. Signal processing is controlled by the above-described signal processing unit 11.

Next, the operation of the apparatus having the structure shown in FIG. 3 will be described. First, the focusing depth of wave transmission is set by an operator from the controller provided on a control panel (not shown in the figure) in order to match the focusing depth with the depth of the region to be examined from the surface of the body around the region. Then, the probe 7 is applied to the region of the object 10 to be examined to begin the ultrasonic scanning.

Figure 4:
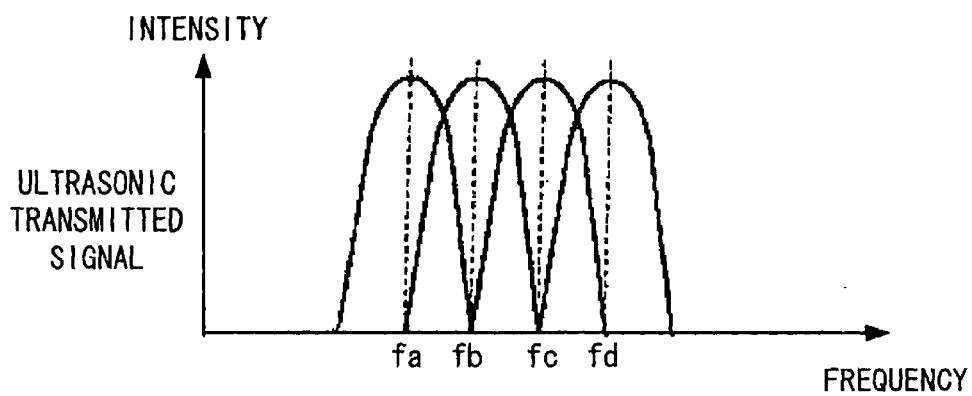
FIG. 4 is a graph showing an example of a plurality of transmitted signals whose frequency characteristics are different from each other.

When the instruction to start the scanning is given from the control panel, the CPU 14 sends an order to each unit, including the pulse generating circuit 1, the transmission delay circuit 2, the modulator 3, the transmission/reception separating circuit 5, the MPX 6, the demodulator 9 and the phasing circuit 10, to start scanning. Upon receiving the instruction from the CPU 14, the pulse generating circuit 1 outputs pulse signals for driving the ultrasonic transducers to the transmission delay circuit 2. In the output line of the transmission delay circuit 2, the outputs of each delay circuit, comprised of m×n delay circuit channels, are connected to each transducer element that forms each of the small transducer blocks 711, 721, 731, 741, respectively, comprising m×n elements, according to operation of the MPX 6. When the pulse signal having a frequency f is sent from the pulse generating circuit 1 to the transmission delay circuits 21, 22, 23, and 24, the pulse signals are delay-controlled by the delay circuits that are provided with delay time data corresponding to the above-set transmission focusing depth by a delay data generation unit (not shown). Then, these delay-controlled pulse signals are output to the frequency modulators 31, 32, 33, and 34. The pulse signals input to the frequency modulators 31, 32, 33 and 34 are subject to frequency modulation in accordance with the frequency modulation data stored in a memory of the control unit 35. Thus, four frequency-modulated signals are used as ultrasonic transmission signals. As shown in FIG. 4, these frequency-modulated signals have, for example, center frequencies of fa, fb, fc, and fd, respectively. The voltage level of the frequency-modulated pulse signals is amplified by the amplifier 4 up to the level required for driving the ultrasonic transducers, and then these pulse signals are input to the MPX 6 through the transmission/reception separating circuit 5. Since the MPX 6 has shifted the output lines of the pulse signals for the transducers as described above, the driving pulses having respective delay time differences are provided to the transducer elements forming the small transducer blocks 711, 721, 731, and 741.

When the driving signals are provided to the transducer elements forming the small transducer blocks 711, 721, 731, and 741, ultrasonic beams are simultaneously transmitted by each of the transducer blocks 711, 721, 731, and 741 to the interior of the object. A part of the ultrasounds transmitted from each small transducer block reflects on the border between tissues having acoustic impedances which are different from each other, and the rest propagate to deeper regions.

Figure 5:
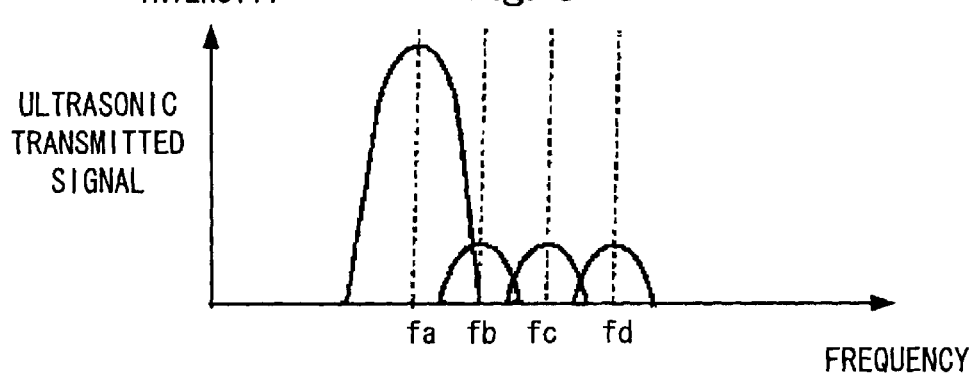
FIG. 5 is a graph showing an example of the signals received by the small-block transducer groups.

The ultrasound that has reflected in the object is received by the probe 10 made up of the two-dimensional transducer array 70. However, the frequencies of the signals received by the small transducer blocks 711, 721, 731, and 741 are varied since ultrasounds having respectively different frequencies are simultaneously transmitted by the small transducer blocks 711, 721, 731, and 741. That is, the signals with a frequency transmitted by the small transducer block 711 and those with other frequencies transmitted by the small transducer blocks 721, 731, and 741 are intermingled in the signals received by the small transducer block 711. Similarly, in the signals received by each of the small transducer blocks 721, 731, and 741, signals with frequencies different from that transmitted by that transducer block are intermingled. As shown in FIG. 5, for example, a small transducer group driven by a transmittal frequency signal fa receives at one time both the echo signals with large intensity transmitted by itself and those with a small intensity having frequencies fb, fc, and fd transmitted by the other blocks. Because of this phenomenon, ultrasonic beams have been conventionally transmitted and received in several directions at one time by a single probe. But, it is difficult to obtain an image suitable for diagnosis by using such echo signals. In accordance with the present invention, the signals with varied frequencies are discriminated by the reception process to be described later so as to extract only those echo signals having the frequency transmitted by that small transducer block.

Figure 6:
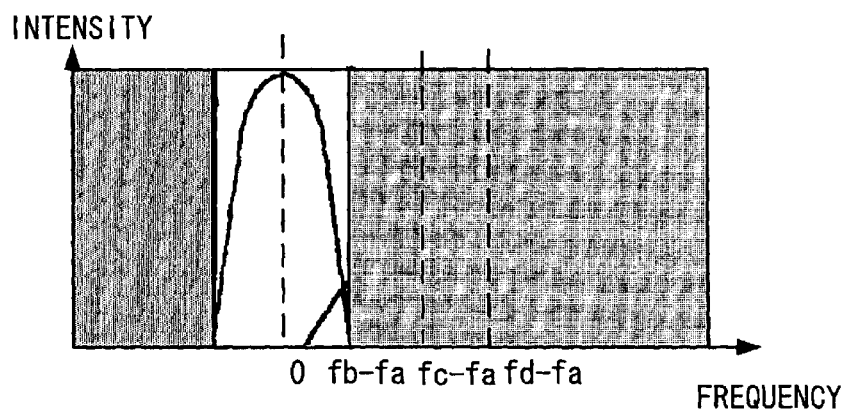
FIG. 6 is a graph showing the state of the demodulated echo signals in which signals having several frequencies are intermingled.

The reflected waves received by the two-dimensional transducer array 70 is converted into electrical signals (echo signals) and input to the reception amplifier 8 through the MPX 6 and the transmission/reception separating circuit 5. Then, these signals are amplified and output to the demodulator 9. This demodulator 9 comprises four demodulators 91, 92, 93, and 94, each circuit having m×n channels. Controlled by the control unit 95, the demodulators 91, 92, 93 and 94 demodulate the signals which have been modulated by the frequency modulator 3. These four circuits 91, 92, 93, and 94 are provided so as to correspond, respectively, to the four frequency modulators 31, 32, 33, and 34. Controlled by the control unit 95, these frequency demodulators 91, 92, 93, and 94 perform this demodulation according to the frequency modulation performed in the corresponding frequency modulator 3. As an example of signal demodulation by the demodulator 9, as shown in FIG. 6, the signals having a frequency fa are extracted with a low pass filter from among the echo signals, in which the echo signals having a frequency fa of strong level and those having frequencies fb, fc, and fd of weak level are intermingled, and the extracted echo signals having a frequency fa are demodulated in order to acquire signals having a frequency f. Incidentally, to deal with a frequency of strong-level echo signals, a high pass filter and a band pass filter may be used instead of said low pass filter.

The echo signals demodulated by the demodulator 9 are input to the four phasing circuits 101, 102, 103, and 104 that are provided in correspondence, respectively, with the small transducer blocks. These phasing circuits 101, 102, 103, and 104 perform a delay time control and adding process on the echo signals of each small transducer block, so as to form a received beam signal for each of the echo signals output by m×n transducers on each small transducer block. Thus, four received beam signals can be acquired at one time.

These received beam signals are subject to detection, logarithmic compression, filtering, and γ conversion in the signal processing unit 11. Thus, processed signals are written on the memory of the DSC 12 and converted into image data. Image data input to the DSC 12 is stored in the memory. The above-described processing represents one cycle of ultrasonic transmission/reception.

After a cycle of transmission/reception is completed, the CPU 14 controls the MPX 6 to move the selected position of the small transducer blocks 711, 721, 731, and 741, as selected respectively within the large transducer groups 71, 72, 73, and 74 in the direction of the arrow, as seen in FIG. 2. After the selected position of the small transducer blocks is moved, the above-described process of ultrasonic transmission/reception is again performed and the echo beams are received at a position next to the beam received in the first transmission/reception cycle in the above direction. The echo signals acquired in the second transmission/reception cycle are also provided to the DSC 12 and stored in the memory. Thus, the selected position of the small transducer block is moved leftward from the initially selected position and the images of two cross sections are obtained by repeating the movement of the small transducer blocks and the ultrasonic transmission/reception. And further, scanning is performed at rapid speed since each cross section is scanned with two ultrasonic beams. After that, the selected positions of the small transducer groups are moved upward by the above-described method to again acquire a pair of cross-sectional images. By repeating this process, the interior of the object is three-dimensionally scanned with ultrasonic beams and a predetermined number of cross sectional images can be acquired.

The three-dimensional image of the diagnostic part is reconstructed with a predetermined number of the above-acquired cross-sectional images. As a reconstruction algorithm for said three-dimensional images, one that is used in an X-ray CT apparatus and an MRI apparatus is employed.

So far, one embodiment of the present invention has been described with reference to the drawings. However, the gist of the present invention is that a plurality of ultrasonic beams having characteristics which are different from each other are transmitted at one time to several points in the interior of the object, and ultrasonic scanning is performed while the position of these ultrasonic beams is moved at each repetition of ultrasonic transmission/reception. Thus, the present invention is not limited to the above-described embodiment.

For example, while outputs of the four transmission delay circuits are subject to frequency modulation in the above-described embodiment, the following alternatives also can be employed as another embodiment. In one alternative, one of the outputs of said transmission delay circuits is not subject to frequency modulation so that the output of the pulse generating circuit is provided as it is to the transducers; while, the rest are frequency-modulated respectively with a different frequency and are provided to the transducers. The small transducer blocks are driven by these signals so as to perform ultrasonic transmission/reception; and, the demodulation of the received signals is performed only on said frequency-modulated signals. In this way, one of the filters of the demodulator can be removed.

Further, in the above-described embodiment, the pulse generating circuit and the frequency modulator are separately provided and the signals from the pulse generating circuit are input to a plurality of the frequency modulators to generate signals each having a respectively different frequency. However, it is possible in another modification to provide signals to transducers with a plurality of the single-type units (pulse generating circuits) and so generate ultrasonic driving pulses having frequencies which are different for each unit. In such an arrangement, demodulation is performed on the received beams, but this should be performed as occasion demands, and it is not always needed.

Further, in the above-described embodiment delay circuits and phasing circuits are provided for transmission and reception. However, if the transmission/reception area of the small transducer block is on the scale of a single transducer, the delay time control for focusing of the transmitted/received ultrasound may be not necessary. And so, these circuits are not indispensable, either.

Further, in the above-described embodiment, four small transducer blocks are selected. However, the number of blocks can be increased. In this way, the scanning time can be further shortened. Further, by also using a technique for generating a plurality of received beams for one transmitted beam of the small transducer blocks, the scanning time can be further shortened.

Further, in the above-described embodiment, each small transducer block is selected as a rectangular block comprising m×n elements. However, the small transducer block is not limited to this form, and it can be selected as a circular block.

According to the present invention, since several transmitted beams are simultaneously transmitted to the interior of the object, ultrasonic three-dimensional scanning can be performed in the interior of the object at rapid speed, as described above. Therefore, an ultrasonic three-dimensional image can be obtained within a short time.

What is claimed is:

1. An ultrasonic diagnostic apparatus comprising:
   an ultrasonic probe in which a plurality of ultrasonic transducers are arranged on a two-dimensional plane or a three-dimensional curved surface;
   a transducer group selecting circuit for selecting a plurality of transducer groups at different positions on said transducer-arranged surface;
   transmitting and receiving means for sending signals having characteristics which are different from each other to each of the transducer groups selected by said transducer group selecting circuit, for transmitting ultrasonic beams all at one time from each selected transducer group to the interior of the object to be examined, and for then receiving echo signals; and
   means for performing three-dimensional ultrasonic scanning of the object by changing the position of the selected transducer groups at every repetition of the ultrasonic transmission/reception by controlling said selecting circuit, and by controlling said transmitting and receiving means to transmit and receive the ultrasonic beams.

2. An ultrasonic diagnostic apparatus comprising:
   an ultrasonic probe in which a plurality of ultrasonic transducer groups are arranged on a two-dimensional plane or a three-dimensional curved surface;
   a transducer group selecting circuit for selecting a plurality of transducer groups to different positions on said transducer-arranged surface;
   transmitting and receiving means for sending signals having characteristics which are different from each other to each of the transducer groups selected by said transducer group selecting circuit, for transmitting ultrasonic beams all at one time from each selected transducer group to the interior of the object to be examined, and for then receiving echo signals;
   means for changing the position of the selected transducer group selected at each repetition of the ultrasonic transmission/reception by controlling said selecting circuit;
   means for extracting the received echo signals that match the characteristics of the signals transmitted by each of said transducer groups from among the echo signals received by that transducer group;
   image composing means for composing the extracted received echo signals to form three-dimensional image data; and
   means for displaying an image from three-dimensional image data output by said image composing means.

3. An ultrasonic diagnostic apparatus comprising:
   an ultrasonic probe in which a plurality of ultrasonic transducers are arranged on a two-dimensional plane or a three-dimensional curved surface;
   a transducer group selecting circuit for selecting a plurality of transducer groups at different positions on said transducer-arranged surface;
   transmitting and receiving means for sending signals having characteristics which are different from each other to each of the transducer groups selected by said transducer group selecting circuit, for transmitting ultrasonic beams all at one time from each selected transducer group to the interior of the object to be examined, and for then receiving echo signals;
   means for changing the position of the selected transducers at each repetition of the ultrasonic transmission/reception by controlling said selecting circuit;
   means for forming received beam signals having characteristics which are uniform from the echo signals received by each of said transducer groups;
   image composing means for composing the received beam signals, the characteristics of which are uniform, to form three-dimensional image data; and
   image displaying means for displaying three-dimensional image data output by said image composing means.

4. An ultrasonic diagnostic apparatus according to any one of claims 1–3 comprising a pulse generating circuit, a transmission delay circuit, and a frequency modulator, wherein an output of said pulse generating circuit is input to said frequency modulator to generate transmitted signals having frequency characteristics which are different from each other.

5. An ultrasonic diagnostic apparatus according to claim 4, wherein one of said plurality of transducer groups is provided with transmitted signals that are not frequency-modulated.

6. An ultrasonic diagnostic apparatus according to claim 4 comprising a demodulator in the receiving circuit of said transmitting and receiving means, wherein echo signals received by said plurality of transducer groups are demodulated by the demodulator and then composed into an image by the image composing means.

7. An ultrasonic diagnostic apparatus according to any one of claims 1–3, wherein said transmitting and receiving means comprises means for forming a plurality of received beams from reflected signals of one transmitted beam transmitted by each transducer group.

* * * * *